(12) United States Patent
Hagberg et al.

(10) Patent No.: US 9,266,900 B2
(45) Date of Patent: *Feb. 23, 2016

(54) ADDITIVES FOR IMPROVED ISOHEXIDE PRODUCTS

(71) Applicant: ARCHER DANIELS MIDLAND COMPANY, Decatur, IL (US)

(72) Inventors: Erik Hagberg, Decatur, IL (US); Erin M. Rockafellow, Decatur, IL (US); Brennan Smith, Decatur, IL (US); Kenneth F. Stensrud, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/437,269

(22) PCT Filed: Oct. 4, 2013

(86) PCT No.: PCT/US2013/063351
§ 371 (c)(1),
(2) Date: Apr. 21, 2015

(87) PCT Pub. No.: WO2014/070370
PCT Pub. Date: May 8, 2014

(65) Prior Publication Data
US 2015/0274746 A1      Oct. 1, 2015

Related U.S. Application Data

(60) Provisional application No. 61/720,466, filed on Oct. 31, 2012.

(51) Int. Cl.
*C07D 493/04* (2006.01)
*A61K 31/34* (2006.01)

(52) U.S. Cl.
CPC .............. *C07D 493/04* (2013.01); *A61K 31/34* (2013.01)

(58) Field of Classification Search
CPC .............................. C07D 493/04; A61K 31/34
USPC .......................................................... 549/464
See application file for complete search history.

(56) References Cited

U.S. PATENT DOCUMENTS 9,145,423 B1 * 9/2015 Sanborn ............... C07D 493/04
2008/0213439 A1 * 9/2008 Fuertes .................. C07B 63/04
426/271

\* cited by examiner

*Primary Examiner* — T. Victor Oh
(74) *Attorney, Agent, or Firm* — William B. Miller (57) ABSTRACT

Reduced color and improved color stability isohexide products are enabled through adding one or more antioxidants to a crude dehydration product mixture from an acid-catalyzed dehydration of a corresponding hexitol.

17 Claims, 4 Drawing Sheets

ADDITIVES FOR IMPROVED ISOHEXIDE PRODUCTS

FIELD OF THE INVENTION

The present invention relates generally to methods for making an internal dehydration product of a sugar alcohol and to compositions including one or more such materials. The present invention relates also to compositions including these materials which can be described as having reduced color and/or as being color stable on storage under generally prevailing storage conditions, and to the methods for making such reduced color, storage stable compositions.

BACKGROUND ART

Sugar alcohols derived from six-carbon sugars (otherwise known as hexitols), such as, for example, sorbitol, mannitol, iditol, and galactitol, have been long known. Particularly in recent years, significant interest has been expressed in the possible use of the internal dehydration products of such materials to displace petroleum-based materials in a number of commercially important applications. Dianhydrohexitols such as isosorbide, isomannide and isoidide, as made by the acid-catalyzed removal of two water molecules from the original internal structure of the corresponding hexitol, have been used or proposed for use in place of petroleum-based monomers such as terephthalic acid, for instance, though particularly in the case of isosorbide a substantial number of additional uses have been, are being or are envisaged to be developed.

As related in U.S. Pat. No. 7,122,661 and in U.S. Pat. No. 8,008,477, however, it has heretofore generally been required for the majority of these uses to apply a purification treatment to the compositions resulting directly from the dehydration step, as these compositions will typically contain each of the stereoisomers isosorbide, isomannide and isoidide, as well as less dehydrated materials such as sorbitan, mannitan, and iditan, a variety of oxidation or degradation products, oligomeric and polymeric byproducts and various other "highly coloured species of a poorly defined nature", see, e.g., U.S. Pat. No. 8,008,477 at column 2, line 35.

As summarized in the aforementioned U.S. Pat. No. 7,122,661 and U.S. Pat. No. 8,008,477, a number of approaches had been suggested previously for obtaining the internal dehydration products (and particularly for obtaining the dianhydrohexitols such as isosorbide especially) in greater purity, for a variety of reasons. Some of these approaches sought improvements in purity through changes to the dehydration process by which the dianhydrohexitols are made, while other approaches involved a form of purification after the dianhydrohexitol compositions are formed.

For example, GB 613,444 describes the production of an isosorbide composition through dehydration carried out in a wafer/xylene medium, followed by distillation and recrystallization from an alcohol/ether mixture.

WO 00/14081 describes distillation and recrystallization from a lower aliphatic alcohol, or distillation alone in the presence of sodium borohydride and in an inert atmosphere.

U.S. Pat. No. 4,408,061 uses gaseous hydrogen halide or liquid hydrogen fluoride dehydration catalysts with carboxylic acid cocatalysts followed by distillation of the crude isosorbide or isomannide compositions thus obtained.

U.S. Pat. No. 4,364,692 briefly mentions prepurification on "ion exchangers and/or activated charcoal", followed, after concentration by evaporation and seeding of crystals of the desired isohexide, by crystallization from water.

Rather than modifying conventional acid-catalyzed dehydration methods or using different, often costly techniques to clean up the direct products of such methods as in the above references, it has also been proposed to generate the dianhydrohexitols by means of certain bimetallic calysts in the presence of hydrogen. For example, EP 380,402 describes synthesis of the dianhydrohexitols by reacting sugar alcohols with hydrogen under pressure and in the presence of particular catalysts based on a combination of copper and a noble metal or gold.

U.S. Pat. No. 6,013,812 observes, however, that these catalysts tended to lose activity fairly rapidly, and proposes an improvement to a conventional acid-catalyzed dehydration wherein acid-stable Ru, Rh, Pd and/or Pt based hydrogenation catalysts and hydrogen are used during the dehydration step.

U.S. Pat. No. 7,122,661 for its part describes a process for obtaining isohexide compositions of 99.5% or greater purity and improved storage stability, without necessarily involving a comparatively costly and low yielding crystallization step from a solvent medium, through using an ion-exchange step followed by a decolorization treatment step. More particularly, a distilled isohexide composition is described as subjected to treatment with at least one ion-exchange means, which can be a mixed bed of anionic resin(s) and cationic resin(s) or a succession of cationic resin(s) and anionic resin(s), followed by treatment with at least one "decolorizing means". The decolorizing means can be activated charcoal in granular or pulverulent form. In certain embodiments, a second treatment, with the decolorizing means is contemplated before the ion-exchange treatment step. Improved stability isosorbide compositions were said to be produced by the process, though the same steps—ion-exchange treatment followed by decolorizing means treatment—were surprisingly said to result in a destabilizing effect when performed in the reverse order.

U.S. Pat. No. 8,008,477, assigned to the same owner as the '661 patent and having one of the inventors of the '661 patent as its sole named inventor, describes an alternate process for preparing a stable isosorbide composition. According to the '477 patent, the stability of an isohexide composition is not necessarily correlated with its purity, and preparation in an inert atmosphere and/or in the presence of sodium borohydride in the dehydration or in the distillation step likewise did not materially improve the stability of these compositions, col. 3, lines 58-67. Rather, "only" the use of specific stabilizing agents in nongaseous form and after the distillation step was helpful for improving the storage stability of isohexide compositions at ambient and moderate temperatures, col. 4, lines 1-14. Suitable "stabilizing agents" are chosen from the group comprising reducing agents, antioxidants, oxygen scavengers, light stabilizers, anti-acid agents, metal-deactivating agents and mixtures of at least any two of such materials, col. 4, lines 48-53. In certain embodiments, an optional further "purification step" was taught following the distillation, an example being the use of both ion exchange and decolorizing means of the type described in the earlier '661 patent.

JP 2006/316025 for its part earlier indicated that the formation of degradation/decomposition products in aged samples of isosorbide was related to auto oxidation of the 1,4-sorbitan monoanhydrohexitol side product and to unspecified "side reactions" involving a solvent (such as water and organic solvents such as xylene and toluene) from the dehydration of sorbitol to make isosorbide. The JP '025 reference prescribes multiple distillations of the crude isosorbide in the absence of a solvent at gradually increasing temperatures and/or at least one such solventless distillation followed by thermal treatment of the isosorbide to reduce the 1,4-sorbitan content of the isosorbide product, with bleaching of the isosorbide product included in each case by treating with ion exchange resins and carbon adsorption.

While the JP'025 reference does thus appreciate that degradation and color formation can proceed front the 1,4-sorbitan monoanhydrohexitol side product, neither the JP'025 reference nor the '477 patent appears to appreciate that the degradation pathways are as extensive as we have found or the corresponding degradation products and unstable intermediate species as numerous as we have found. Not surprisingly, we have found that the approaches takers and the corrective measures proposed by the '477 patent and the JP'025 reference are correspondingly incomplete or even counterproductive.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

With this in mind, the present invention in part relates to the discovery that, contrary to the teachings of the '477 patent, a number of materials suggested as suitable "stabilizing agents" but not exemplified therein were in fact not very effective for providing reduced color, color stable isohexide compositions when actually tried. We further found, also contrary to the teachings of the '477 patent, that antioxidants added prior to the distillation step can provide a reduced color, stable isohexide product. In addition, use of the antioxidants prior to the distillation step enables higher yields of such a reduced color, stable isohexide product in that volatile color bodies which would otherwise form in the course of distillation and co-distill with the isohexide under more aggressive conditions can be reduced; consequently, the more aggressive distillation conditions can be used and greater yields realized from the distillation, without a corresponding increase in color bodies that would have to be removed or acted upon to ultimately provide the desired low color, stable isohexide product.

Thus, in one aspect the present invention concerns a distillable composition of matter comprised of a crude dehydration product mixture from the acid-catalyzed dehydration of one or more hexitols and one or more antioxidant additives.

In another aspect, a process is provided for making reduced color, stable isohexides including an acid-catalyzed dehydration of one or more hexitols to provide a crude dehydration product mixture, adding one or more antioxidant additives to the crude dehydration product mixture, then further processing the additive-modified crude dehydration product mixture to produce a product enriched in at least one isohexide compared to the crude dehydration product mixture.

DESCRIPTION OF EMBODIMENTS

In a first aspect as just mentioned, the present invention concerns antioxidant additives to a crude dehydration product mixture from the acid-catalyzed dehydration of one or more hexitols, and the resultant distillable compositions of matter.

Whereas the '477 patent indicates that the color stability of an isohexide composition is "not necessarily" related to its purity, we have in fact identified a number of materials which are or may be present in the crude dehydration product mixture and have confirmed that these impurities do relate (directly or indirectly) to the formation of color in a conventional 100 percent molten finished isohexide product or in a conventional 85 weight percent solution product.

For the preparation of isosorbide from sorbitol by acid-catalyzed dehydration, these materials can include organic and inorganic salts, acids (for example, formic acid and levulinic acid), acid esters (e.g., sulfate esters from a sulfuric acid catalyzed dehydration step, phosphate esters from phosphoric acid catalyzed dehydration and in general the acid esters from a given oxygen acid catalyzed dehydration step) and their conjugate bases, furanics (e.g., 2-acetylfuran, 5-methylfurfural and various five carbon furanics), oligomeric and polymeric materials from, e.g., acid-catalyzed condensation of various ether functionalized impurities in a crude isosorbide product.

Figure 3:
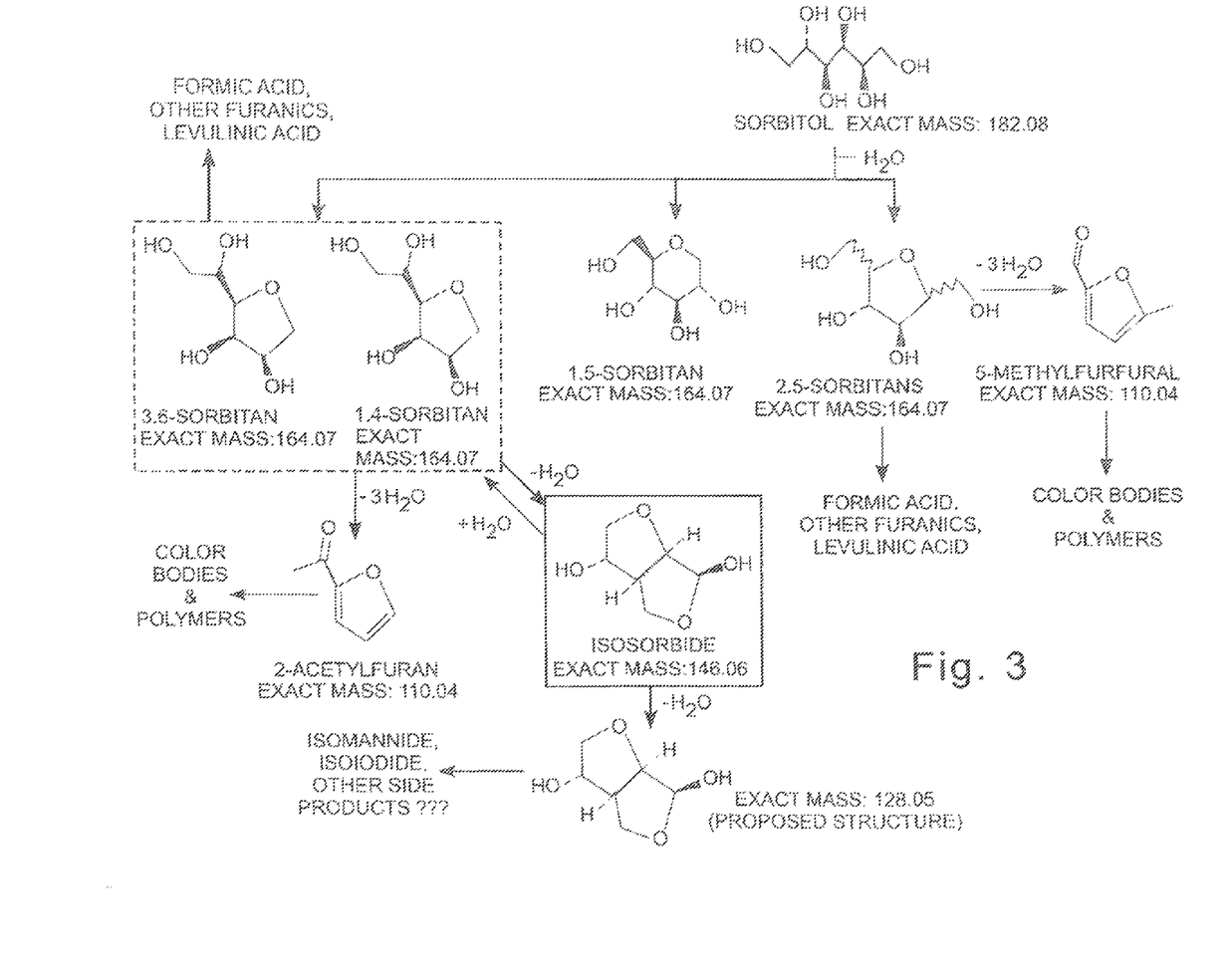
FIG. 3 depicts a proposed dehydration and degradation reaction pathway for a sulfuric acid-catalyzed dehydration of sorbitol, based on information obtained by liquid chromatography/mass spectrometry, gas chromatography/mass spectroscopy and by ion chromatography of a crude dehydration product.

More particularly, without being bound and without limiting the present invention in any sense, FIG. 3 depicts a number of materials which have been identified or are believed to be present in the crude dehydration product mixture from a sulfuric acid-catalyzed dehydration of a commercially available sorbitol product and postulates the pathways by which these materials may be formed, based on the confirmed presence of compounds of a given molecular weight as indicated by gas chromatography/mass spectroscopy and, as to the specifically identified sulfate esters, by liquid chromatography/mass spectrometry, as well as based on prior experience with the dehydration of sorbitol.

As will be evident to those skilled in the art on considering the complexity of the illustrated postulated pathways, not all materials present in the crude dehydration product mixture have been identified for FIG. 3 or even attempted to be identified nor quantified, and different (but generally similar) species can be expected in the dehydration of other hexitols by other processes or means than by the use of sulfuric acid. As well, upon distillation for other further processing) of a crude dehydration product mixture of this character, still other compounds can be expected to form in varying degrees dependent on the particular distillation conditions employed, for example.

Figure 4:
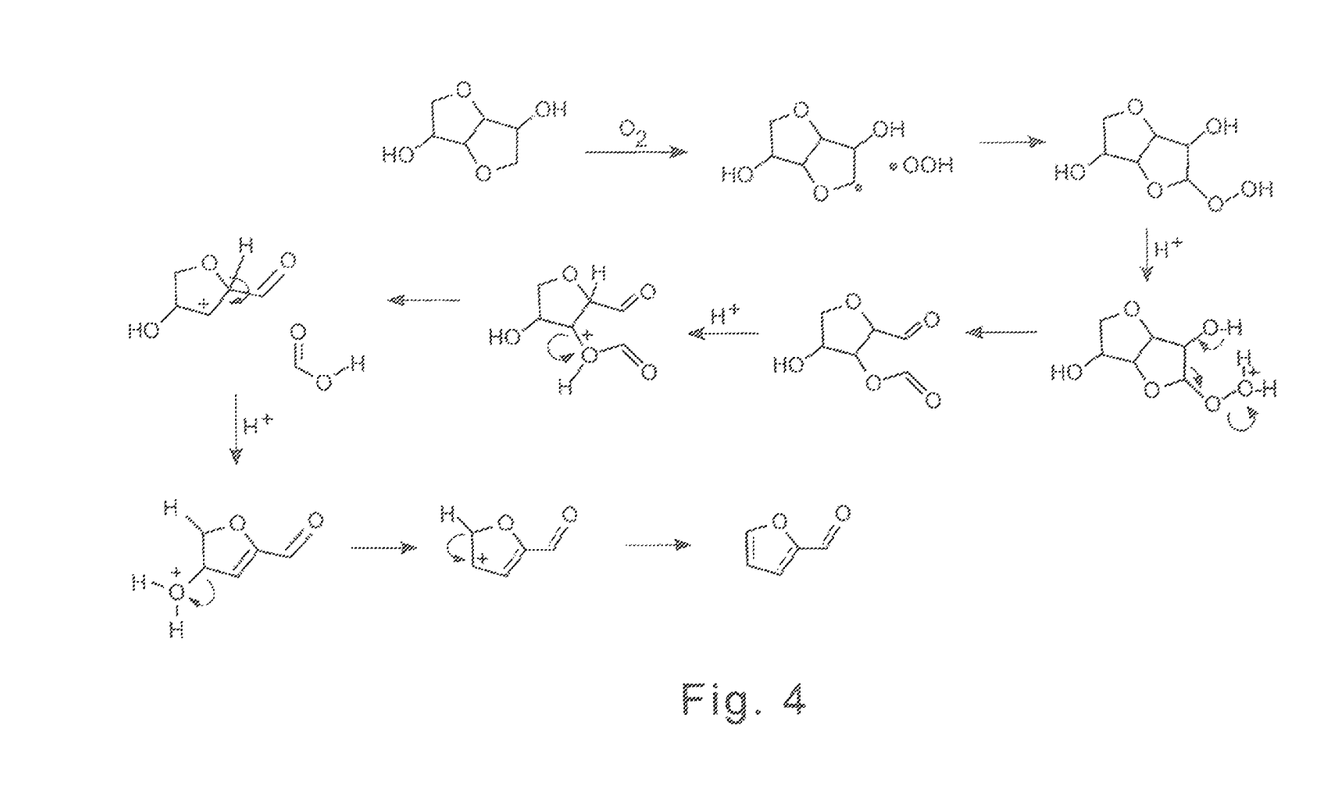
FIG. 4 depicts a proposed pathway for the auto-oxidation of isosorbide to produce furfural and formic acid.

Further, while the materials present in a crude dehydration product mixture at a particular point in the overall process of making and finishing an isohexide product and/or while some of the compounds formed thereafter in a distillation step, in further processing or even after a certain time in storage may not result in unacceptable color, those skilled in the art will appreciate that ongoing chemical changes that occur in a particular finished isohexide product over a period of time under the storage conditions that can be expected to be experienced by the product, can nevertheless result in the development of unacceptable color in the finished isohexide product. Particularly in regard to the present invention, it was in addition appreciated that more formic and other organic acids were being formed than could be accounted for by the sorbitans (including the various other sorbitans in addition to the 1,4-sorbitan deemed culpable by the JP'025 reference), and that these acids once formed would then catalyze a cascading series of dehydration reactions producing a variety of furanic, colored and unstable species. Without being limiting in any sense of the present invention, at least some of these are postulated to occur through an auto-oxidation mechanism; a proposed pathway is illustrated in FIG. 4 whereby on exposure to the oxygen in air over time isosorbide can degrade to form furfural as well as formic acid.

In any event, the sources and pathways by which color formation occurs in an isosorbide product are certainly more extensive and more numerous, respectively, than had previously been indicated by either the JP'025 reference or either of the '477 and '661 patents.

Despite all of these complexities, we nevertheless consider that certain measures will be effective for producing reduced color and/or improving the color stability of a given finished isohexide product, and expect that those skilled in the art will be well able based on the guidance provided herein and especially based on the working examples below to employ those additives and to optionally undertake additional steps described below and in companion applications to the present application, in order to realize a certain reduction in color and/or improvement in color stability on storage of a particular finished isohexide product.

The '477 patent contemplates a number of disparate types of "stabilizing agents", but includes very little discussion of the sources and mechanics of color formation and not many examples for or from within the disparate stabilizing agent types—sodium borohydride (described under "reducing agents"), morpholine (described under "antioxidants"). BHT (described under "antioxidants"), vitamin C (described under "antioxidants"), NaOH (described under "anti-acid agents"), $NaBO_2$ (described under "anti-acid agents") and $Na_2HPO_4$ (described under "anti-acid agents") comprising all of the exemplified additives providing compositions deemed "stable", having both a formic acid content of less than 5 ppm and an overall content of monoanhydrohexoses of less than 50 ppm, expressed on a dry weight basis relative to the dry weight of the composition as a whole.

While the '477 patent does contemplate that the claimed stabilizing agent additives can achieve stable compositions when acting upon an isohexide-enriched distillate, see, e.g., col. 4, lines 23-24, it is indicated to be advantageous for the distillate to also be subjected to a purification step b) which includes treatment with at least one of activated charcoal or adsorption resins, col. 7, lines 43-45, or ion exchange resins, col. 7, lines 52-54, and "particularly advantageous" for the distillate subjected to such a purification step and then treatment with a stabilizing agent to already have a formic acid content less than 20 ppm and of monoanhydrohexoses of less than 200 ppm relative to the dry weight of the predominant isohexide in the distillate, col. 8, lines 14-22. Application of the claimed stabilizing agent additives is advantageously carried out in a liquid medium, at a temperature at least equal to the softening or melting temperature of the principal isohexide product in the distillate but less that 140 degrees Celsius, col. 8, lines 35-40. The assignee of the '477 patent further states that it "thinks that it may be advantageous for the said improving agent to have minimal solubility in water and/or in the desired internal dehydration product", col. 8, lines 47-50.

Against the background of the '477 patent and the teachings of the JP'025 reference, we mixed isosorbide (100% molten) with a number of different additives, including antioxidants (BHT, tert-butyl-hydroxyquinone (TBHQ)) as well other materials ($K_2CO_3$, CaO, $NaHCO_3$, NaOH, $CaOH_2$, ammonium benzoate, $Ca(H_2PO_4)_2$, $NaH_2PO_4$), and heated the combination for from 1-2 hours at 200 degrees Celsius. We found that generally any ionic additive, whether buffers, acids or bases, tended to decrease the color stability of isosorbide as indicated through accelerated aging tests. Further, functional groups on the stabilizer additives greatly affected performance. Stabilizers containing amine or quinone functionality (for example, t-butyl-hydroxyquinone (CAS 1948-33-0), methylhydroquinone (CAS 95-71-6), 2,5-di-tert-amylhydroquinone(CAS 79-74-3), 4,4'-bis(α,α-dimethylbenzyl)diphenylamine (CAS 10081-67-1), 2,5-di-tert-butylhydroquinone (CAS 88-58-4)) would often exhibit low color initially, but were not color stable over time, even at room temperature in some cases. Carboxylic acid functionalized stabilizers (for example, 6-hydroxy-2,5,7,8-tetramethylchromane-2-carboxylic acid (CAS 53188-07-1), 2-ethylhexylsalicylate (CAS 118-60-5)) showed good solubility in a conventional 85% solution product but appeared to promote color formation, developing color faster than an unstabilized control. Stabilizer additives with bulky alkyl substituents (for example, α-tocopherol (CAS 10191-41-0) and 4,4'-butylidenebis(6-t-butyl-m-cresol) (CAS 85-60-9)) showed initial promise, but over time tended to migrate out from a conventional 85% solution product. Stabilizers that were other than, antioxidants—a borate buffer or isosorbide diglycidol ether as an acid scavenger—were ineffective in the absence of an antioxidant.

Without being limiting of the present invention in any way, we thus consider that it is likely the first step in the formation of color in isosorbide is an autooxidation step, and that the formation of formic acid (through the postulated pathways shown in FIG. 3 and/or in FIG. 4 or through other routes) rapidly contributes to the formation of color, through rapid dehydration leading to a derivative set of further highly colored decomposition products.

Accordingly, recognizing as this first autooxidation step occurs and as organic acids such as formic acid are formed that any additional exposure to heat over time (as, for example, in the thermal treatment proposed by the JP'025 reference) will be counterproductive, according to the present invention in a first, broad aspect, one or more antioxidant additives are combined with a crude dehydration product mixture from an acid-catalyzed dehydration of one or more hexitols, prior to the distillation of the crude dehydration product mixture (step (a) in the process of the '477 patent) to provide a distillate enriched in a desired isohexide product. Preferably, in contrast to the preferences expressed in the '477 patent the antioxidants employed by the present invention have sufficient volatility to at least partially co-distill with the isohexide and are sufficiently soluble in the isohexide under room temperature conditions, so that the finished isohexide product retains an antioxidant component after distillation to help protect against the autooxidation and further degradation of the isohexide product on storage. Preferably, enough of the one or more antioxidants are retained to provide color stable compositions as specified herein, in both a conventional 100% molten product form as well as an 85% solution product.

Our preferred antioxidants for color-stabilizing isosorbide were hindered phenols containing one or more methoxyl groups and no other functional groups, other than alkyl groups. Examples of our preferred antioxidants for color-stabilizing conventional 100% molten and 85% solution isosorbide products include di-tert-butyl-4-methoxyphenol (or DTMP, CAS 128-37-0), butylated hydroxyanisole (BHA, mix of 2- and 3-tert-butyl-4-hydroxyanisoles, CAS 25013-16-5). 2,6-dimethoxy-4-methylphenol (DMMP, CAS 6638-05-7) and 2,6-dimethoxyphenol (DMP, CAS 91-10-1). Of these, most preferred are BHA and DMMP.

By way of further explanation, each of these co-distilled with isosorbide to a degree that they could be recovered in the distillate at a yield of at least 50% (50%, 63%, 84% and 64%, respectively), provided a clear distillate (without cloudiness or solids) having an initial APHA color value by ASTM D1209 of 20 or less (15.6, 14.1, 13 and 18.7, respectively, in the neat distillate), and showed continued good solubility in an 85% solution product initially and over time. We additionally considered that the APHA color of a neat isosorbide distillate containing these additives should preferably be less than 200 after accelerated aging at 85 degrees Celsius for 4 weeks, and for an 85% solution of the distillate should be less than 250 after accelerated aging under these conditions. Isosorbide distillates including BHA and DMMP were color stable to an extent that these criteria were met, whereas isosorbide distillates including DTMP and DMP met the criterion for either the neat distillate or the 85% solution product hut not for both.

Based, on the above guidance and the examples following, other antioxidants or combinations of antioxidants may be evident to those skilled in the art as useful for isosorbide or for a particular isohexide or combination of isohexides, more generally, dependent on the initial color and color stability requirements of a 100% molten or 85% solution product application. In general, however, we consider that the antioxidant or antioxidants should co-distill with the particular isohexide or combination of isohexides to an extent whereby preferably at least 50% of the antioxidant or antioxidants collectively remains with the distillate, while initial color and accelerated aging color values as well as the solubility for the near-term and over time in an 85% solution can vary as just indicated based on the finished product and application under consideration. Nevertheless, it will be well within the capabilities of those skilled in the art to determine which antioxidants best meet the requirements of a given finished product and application.

The amount of antioxidant(s) employed can correspondingly vary from one finished product and application or end use to other finished products and/or applications. As a general guideline, however, it is expected that the amount of antioxidant(s) employed can range from as little as 10 parts per million by weight of the remainder. In other embodiments, the amount of antioxidant(s) can be from 100 parts per million by weight. In still other embodiments, the amount of antioxidant(s) can be from 300 parts per million by weight of the remainder. Generally the amount added will be just sufficient to provide the improvements in color and in color stability that are needed for a given end use application and for a given isohexide, whether used alone in the context of an otherwise conventional process for making the isohexide or whether used in combination with one or both of commonly-assigned U.S. Patent Application Ser. No. 61/720,453, filed Oct. 31, 2012 for "IMPROVED METHOD OF MAKING INTERNAL DEHYDRATION PRODUCTS OF SUGAR ALCOHOLS", and commonly-assigned U.S. Patent Application Ser. No. 61/720,457, filed Oct. 31, 2012 for "HYDROGENATION OF ISOHEXIDE PRODUCES FOR IMPROVED COLOR AND/OR COLOR STABILITY", as these optional supplemental measures are described below.

While particular color requirements may vary as just mentioned, in general, it is expected that finished 100% molten and 85% solution isohexide products made at least in part by means of the present invention will demonstrate an initial APHA color as determined in accordance with ASTM D1209 of 20 or less, preferably 15 or less and especially 10 or less. Preferably, the color stability of these compositions will be such that, as mentioned above, after accelerated aging at 85 degrees Celsius for four weeks, the APHA color of a 100% molten product will still be less than 200, and for an 85% solution product will still be less than 250.

The manner in which the present invention (and optionally including the measures described in either or both of the commonly-assigned applications) may be employed can probably best be illustrated by reference to a known process for making an isohexide. As described above, a number of processes have been developed or proposed for making the isohexides from the corresponding sugar alcohols (and/or monoanhydrosugar alcohols). The manufacture of isosorbide from sorbitol has been particularly of interest. In addition to the processes described in the patents referenced above, commonly-assigned U.S. Pat. No. 6,849,748; U.S. Pat. No. 7,420, 067; and U.S. Pat. No. 7,439,352 are examples of processes that have been developed for making isosorbide from sorbitol, and provide a useful, non-limiting context for describing the present invention.

Figure 1:
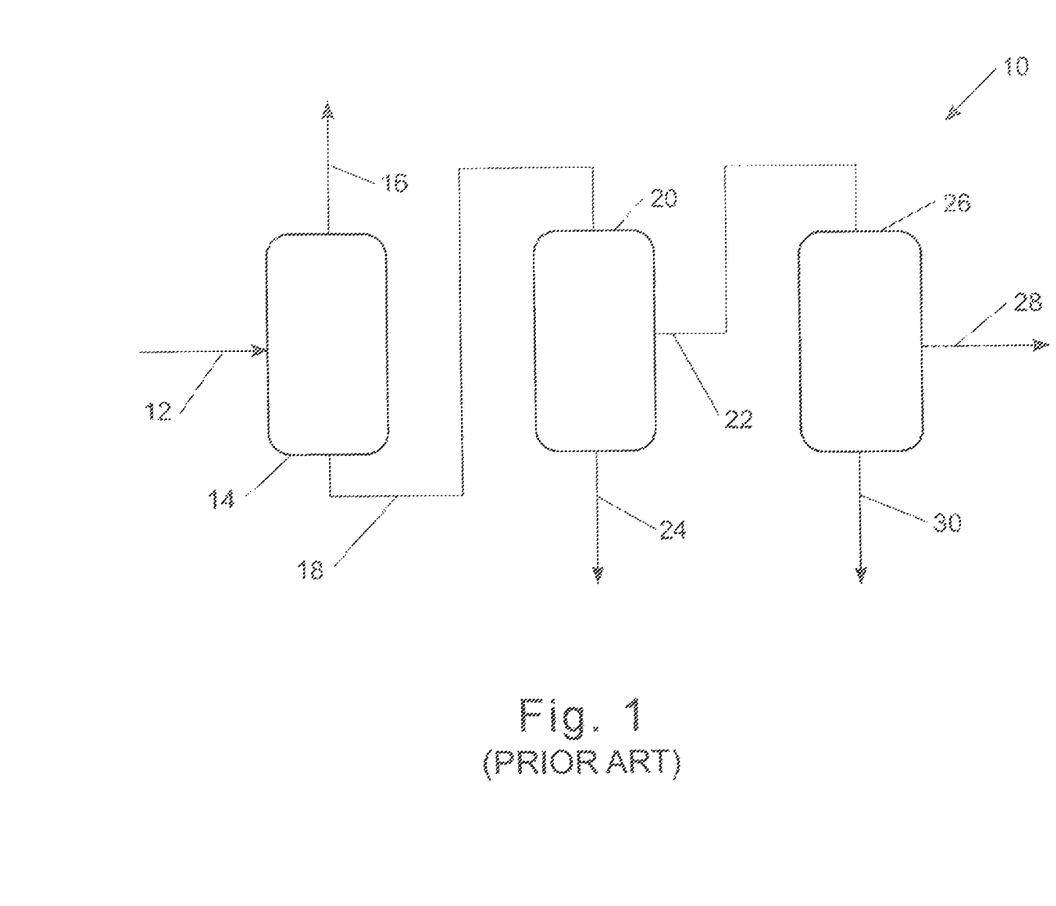
FIG. 1 is a schematic diagram of a process for manufacturing isosorbide from sorbitol in accordance with U.S. Pat. No. 7,439,352.

Turning now to FIG. 1, in a process 10 as originally described in the '352 patent, sorbitol is supplied as indicated by reference numeral 12 to reactor 14. The sorbitol 12 is first heated to a molten state, then is dehydrated in the reactor 14 in the presence of a catalyst for facilitating the dehydration to isosorbide, producing a water effluent 16 and a dehydration product mixture 18 including isosorbide. The dehydration product mixture 18 is then subjected to a first distillation in a first distillation apparatus 20 to form a first isosorbide distillate 22 and a first distillate bottoms 24. The first isosorbide distillate 22 is then subjected to a second distillation in a second distillation apparatus 26 to form a purified isosorbide product 28 and a second distillate bottoms 30.

More particularly, in the first step of the process 10 of FIG. 1, the sorbitol is melted by standard methods that are known in the art. For example, the sorbitol can be melted by placing it in a 3-neck round bottom flask equipped with an agitator, temperature probe, and vacuum line. Preferably, the sorbitol is heated to at least 100 degrees Celsius to 200 degrees Celsius. For sorbitol powder, to provide a specific example, the preferred melting temperature is from 98 degrees Celsius to 105 degrees Celsius, while an even more preferred melting temperature is from 98 degrees Celsius to 100 degrees Celsius. Once molten, the sorbitol is subject to stirring.

A catalyst that will facilitate the dehydration of the sorbitol is then added to the molten starting material. Typically acid catalysts have been used to facilitate the dehydration of sugar alcohols such as sorbitol including for example soluble acids, acidic ion exchange resins, and inorganic ion exchange materials. Sulfuric acid, phosphoric acid, p-toluenesulfonic acid, and p-methansulfonic acid are given as examples of preferred soluble acids that may be used, though one of skill in the art would recognize that other soluble acids with similar properties would be useful as well.

Zeolite powders are examples of inorganic ion exchange materials that could be used; specifically an acidic zeolite powder such as a type ZSM-5 ammonium form zeolite powder may be used. Examples of zeolite powders said to be useful include, but are not limited to, CBV 3024 or CBV 5534G (both available from Zeolyst international), and/or T-2665 or T-4480 (both available from United Catalysis, Inc.). One of skill in the art would recognize that other zeolite powders with similar properties may be useful though not specifically listed here.

A sulfonated divinylbenzene/styrene co-polymer acidic ion exchange resin provides an example of a possible acidic ion exchange resin catalyst. Examples include, but are not limited to, AG50W.X12 from BioRad Laboratories, Amberlyst 15 or Amberlyst 35 from Rohm & Haas, RCP21H from Mitsubishi Chemical Corp., and Dowex 50Wx5 (Dow Chemical Co.). The sulfonated divinylbenzene/styrene co-polymer acidic ion exchange resin, Amberlyst 35, is indicated as a particularly preferred resin for the production of isosorbide from sorbitol. One of skill in the art would be aware of other acidic ion exchange resins with similar properties that could be used.

The amount of catalyst used is indicated as generally being on the order of from 0.01 equivalents to 0.15 equivalents by weight. A preferred amount of catalyst is 0.1 equivalents by weight.

The dehydration in the '352 patent can be carried out under a vacuum, at elevated temperatures, and with stirring of the reaction mixture. The vacuum can range over a pressure of from 0.05 Torr to 40 Torr, with preferred pressures of from 1 Torr to 10 Torr. As a specific example, a preferred pressure for the dehydration of sorbitol to isosorbide is from 1 Torr to 10 Torr. The temperature for the dehydration can be from 90 deg. C. to 140 deg. C. In certain embodiments, the dehydration temperature can be from 98 deg. C. to 130 deg. C., especially, from 120 degrees Celsius to 130 degrees Celsius. The dehydration can be carried out over a period of approximately 2 hours at such temperatures. The water can be pulled off of the melted sorbitol/catalyst mixture under a vacuum of from 1 Torr to 10 Torr. The dehydration reaction is preferably performed in a reactor which can run in a batch or continuous mode. In embodiments wherein the acid catalyst is a solid acid catalyst (e.g., acidic ion exchange resin), the reactor can preferably hold or contain baskets to which the solid acid catalyst can be added.

Following the dehydration procedure, the resultant dehydration product mixture 18 is purified. In one embodiment, a vacuum distillation is used, for example using a wiped film evaporator with an external condenser or using a short path distillation device including an internal condenser. One example of a wiped film evaporator apparatus is a vertical agitated thin-film processor. Advantages of using a wiped film evaporator include handling of viscous solutions, improved product purity, and low residence time, which leads to a reduction or elimination of product degradation. Specifically with respect to production of isosorbide from sorbitol, use of a wiped film evaporator was said to provide approximately an 80% yield on distillation, negligible water loss during distillation (which results in reduced polymerization), and to provide for further recovery of isosorbide and sorbitan from the residue. The distillation process results in a first isosorbide distillate 22.

The pot temperature and vacuum used for the first distillation apparatus 20 can vary, but vapor temperatures of from 140 degrees Celsius to 190 degrees Celsius are indicated as preferred. More preferred vapor temperatures are from 160 degrees Celsius to 170 degrees Celsius, especially from 165 degrees Celsius to 170 degrees Celsius. The vacuum pressure can be from 0.05 Torr to 40 Torr, preferably being from 1 Torr to 10 Torr. For the vacuum distillation of isosorbide, a vacuum pressure of from 1 Torr to 10 Torr, a pot temperature of 180 degrees Celsius, and a vapor temperature of from 160 degrees Celsius to 170 degrees Celsius are said to be most preferred. Alternative purification methods such as filtration or the addition of activated charcoal with subsequent crystallization are also mentioned as useful.

The first isosorbide distillate 22 is then preferably subjected to a second vacuum distillation in a second distillation apparatus 26, for example, by means of a second wiped film evaporator. The second wiped film evaporator can be of the same type as, or different than, the first wiped film evaporator. The conditions (e.g., vacuum pressure and temperature) of the second vacuum distillation can be the same as, or different than, the conditions of the first vacuum distillation, the parameters of which are described above. The use of two film evaporators is said to allow for production and purification of isosorbide without the use of potentially harmful organic solvents.

In an alternate embodiment described in the '352 patent, the first isosorbide distillate 22 is subjected to melt crystallization wherein the first isosorbide distillate 22 is heated until molten (isosorbide's melting point is about 65 degrees Celsius), and then cooled over time until the crystallization point is reached, but not so much that the material solidifies. In fact, a slurry-like consistency is preferred, so that the material can be centrifuged. As used herein, the term "slurry-like consistency" refers to a material that is a mixture of liquid with several finely divided particles. The centrifugation is performed at a relatively high speed for a relatively short period of time in order to avoid solidification of the material, and also to avoid having the desired isosorbide product drawn off with the impurities. For example, the centrifugation can be performed at 3000 to 4000 rpm for 5 minutes, though those skilled in the art will appreciate that the duration of centrifugation will ideally vary depending on the amount of material to be purified. The resultant isosorbide in any case is indicated as being at least 98% pure, and in most cases being greater than 99% pure (depending upon the solidity of the "slurry").

Alternatively, the '352 patent, also contemplates that the first isosorbide distillate 22 can be subjected to solvent recrystallization. Solvents mentioned as useful include, but are not limited to, acetone, ethyl acetate, and low molecular weight alcohols such as ethanol and methanol.

In still another embodiment mentioned in the '352 patent, further purification of the first isosorbide distillate 22 can involve subjecting the first distillate 22 to a solvent wash, followed by filtration. Preferably, the solvents are cold, for example, having a temperature of 0 degrees Celsius to 23 degrees Celsius. Solvents mentioned included acetone, ethyl acetate, and low molecular weight alcohols such as ethanol and methanol. Filtration was described as carried out by means well known in the art.

In one embodiment of a process according to the present invention, a process according to any of the aforementioned embodiments described in U.S. Pat. No. 7,439,352 is modified to include the addition of one or more antioxidants to the crude dehydration product mixture, prior to its further processing to yield a product enriched in at least one isohexide compared to the crude dehydration product mixture, for example, by successive distillation steps as shown in FIG. 1.

Figure 2:
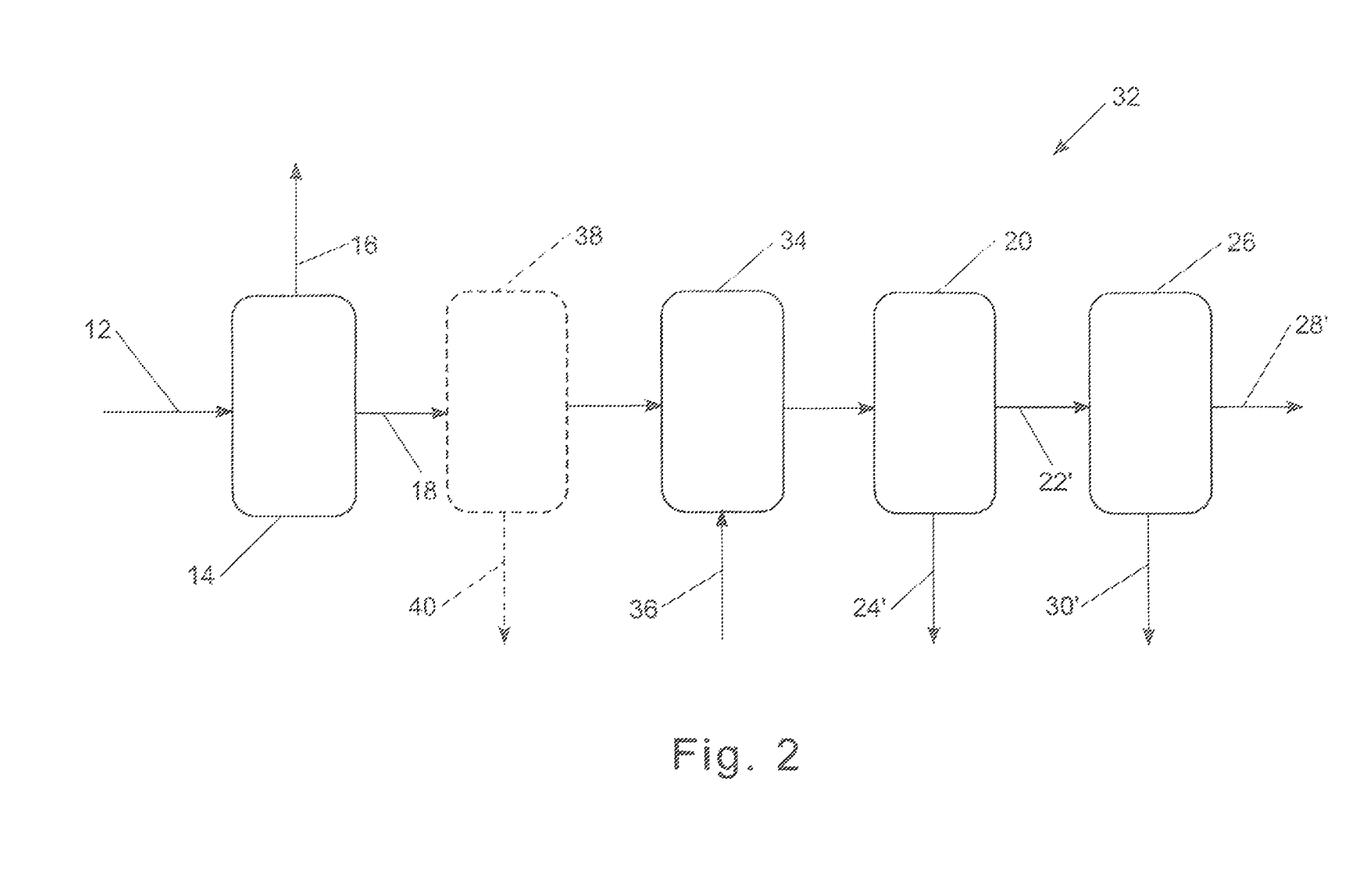
FIG. 2 is a schematic diagram of the process of FIG. 1, modified in accordance with the present invention to include the addition of one or more antioxidant additives to a crude dehydration product mixture.

Turning now to FIG. 2, an example of such a modified process 32 is schematically illustrated, in which an antioxidant additive addition step 34 is included along with an optional crude isosorbide impurity removal system 38, with other elements of the process 32 being as previously described in respect of FIG. 1 (as indicated by the use of the same reference numbers). Where the optional crude isosorbide impurity removal system 38 is omitted, the antioxidant additive(s) are added to the crude dehydration product mixture 18, but preferably an isosorbide impurity removal system 38 is used to remove ionic species 40 from the crude dehydration product mixture 18 before the antioxidant additive(s) are added.

The isosorbide impurity removal system 38 can fundamentally involve the application of ion exchange, ion exclusion or both of ion exchange and ion exclusion methods to the crude dehydration product mixture 18 for removing impurities mentioned above and in connection with FIG. 3, namely, solubilized organic and inorganic salts, formic and levulinic acids, formate and levulinate esters, as well as other acid esters from an oxygen acid catalyzed dehydration step and their conjugate bases, furanics, oligomeric and polymeric materials and related degradation intermediates or precursors, substantially as described in commonly-assigned U.S. Patent Application Ser. No. 61/720,453, filed Oct. 31, 2012 for "IMPROVED METHOD Of MAKING INTERNAL DEHYDRATION PRODUCTS OF SUGAR ALCOHOLS". Preferably, by such means and by optional additional means, such as carbon or resin adsorption following the ion exchange, ion exclusion or ion exchange/exclusion means, substantially all of at least the ionic species from the crude dehydration product mixture 18 and more preferably substantially all of the aforementioned species or precursors of such species tending to give rise to color formation in a finished isohexide product on storage are removed.

The crude dehydration product mixture 18 (minus the impurities 40) is then filtered to remove any of the resin(s) and carbon(s) from the system 38 that may be carried over from the system 38, then receives the one or more antioxidant additives (indicated by 30) in addition step 34 before being further processed to ultimately yield a finished isosorbide product (28' in FIG. 2) which is enriched in the desired isosorbide material compared to the crude dehydration product mixture 18. In the particular illustrative embodiment shown schematically in FIG. 2, initially water is removed in a dewatering step. While the incorporation of co-distilling antioxidant additives in the process of the present invention enables more forceful distillation conditions to be used to recover more of the desired isohexide(s) than would be possible according to the teachings of the '447 patent, nevertheless, in that color develops more readily with the development of a heat history in the making and purification of these isohexides, preferably the dewatering as well as the subsequent refining involve lower temperatures and higher vacuum. Enrichment in the isosorbide after the dewatering step can thus be conventionally achieved by any of the known refining methods, for example, through successive distillations in first and second distillation apparatus 20 and 26, respectively, though the first and second distillation apparatus 20 and 26 preferably make use of thin or wiped film evaporation as in FIG. 1 to minimize further heat history on the desired isosorbide product 28'.

The present invention is further illustrated by the following examples:

Example 1

A 500 mL boiling flask equipped with a Teflon stir bar was charged with 100 g of ion-exchanged (strong acid cation/strong base anion-exchanged), dewatered, molten isosorbide. While stirring, 40.02 mg of 2,6-di-tert-butyl-4-methoxyphenol (DTMP), previously dissolved in 2 mL of absolute ethanol, was added via pipette, indicating the DTMP concentration as 400 ppm in the matrix. The flask was then outfitted with a still head, condenser, and receiver, placed under a vacuum of <2 torr, and placed in a digitally controlled oil bath. The bath was gradually heated to 190 degrees Celsius while maintaining a vacuum. At a bath temperature of approximately 155 degrees, isosorbide began to distill (vapor temperature of 150 deg C.). Continuous distillation occurred for approximately 30 minutes. 45.6 grams of clear, colorless isosorbide was collected, whose APHA color was measured as 6. Quantitative analysis by UPLC determined the concentration of DTMP in the distilled isosorbide to be 503 ppm.

About, an 11 gram sample of the isosorbide distillate was added to a glass tube and capped with a septum. The glass tube was then submerged in a 200° C. oil bath for 1 hr under air. Approximately 0.5 g of the heated distillate sample was subsequently diluted with 2 mL of water and analyzed by UV/vis to obtain an APHA color value. An APHA color of approximately 250 was observed, compared to an APHA value for a distillate sample absent the DTMP additive that was offscale (>500).

The DTMP-stabilized distillate was further tested for color storage stability by thermal aging over a more extended period of time, in particular, by preparing typically five 10 mL headspace vials of each of the neat distillate and an 85% solution of the distillate in water in 0.5 gram sample portions. One vial of the set of five for the neat distillate or the 85% solution was set aside as the "time zero" data point. The time zero sample was diluted with 2 mL of water and analyzed.

For the neat distillate, the APHA color of the time zero sample was less than 20 by UV/vis. All other decomposition products were less than 5 ppm. The four other vials of the neat distillate were then placed in an 85 deg C. oven trader air, and one vial was removed at 7 days, another at 14 days, another at 21 days, and the last of the four at 28 days. Once removed from the oven, each sample was allowed to cool to room temperature and diluted with 2 mL of water. The sample was then analyzed by UV/vis, UPLC, LC-MS, and GC. After 28 days, APHA color, measured as a 20% solution, was only 28. Furfural and formic acid were measured at 18 ppm and 39 ppm, respectively.

Samples of unstabilized isosorbide were prepared in same manner and monitored as a control. Initially, the control sample contained less than 5 ppm of analyzed decomposition products and had an APHA color less than 20. The unstabilized sample aged for 28 days showed furfural and formic acid concentration was 69 ppm and 12,253 ppm, respectively, and the APHA color value was again offscale (>500).

For the 85% solution, by comparison, the APHA color values of the time zero and day 28, final diluted (20%) DTMF-stabilized solutions were 0 and 150, respectively. A similarly diluted (20%) control without stabilizer included showed an APHA of 0 initially but was offscale (>500) after 28 days. Furfural concentration was less than 5 ppm in all samples initially, 88 ppm in the final DTMP-stabilized sample, and 323 ppm in the unstabilized final sample. Formic acid concentrations of the final samples were 250 ppm in the DTMP-stabilized 85% isosorbide and 4.119 ppm in the unstabilized 85% isosorbide.

The 85% isosorbide solution seemed to degrade and form color more quickly than the neat solutions. A notable difference in decomposition products was observed in the formation of 5-hydroxymethylfurfural (HMF). In the neat unstabilized solution, this compound formed at very low levels (<20 ppm); however, in the unstabilized 85% solution HMF formation was up to 600 ppm. HMF formation in both the neat, and 85% DTMP-stabilized samples was greatly suppressed (<5 ppm).

Example 2

In this as in subsequent examples, a quantity of an antioxidant under evaluation was dissolved in 1-2 mL of absolute ethanol and then added via pipette to a crude isosorbide mixture which had been treated previously to remove ionic species therefrom. Amounts were set so that the concentration of the antioxidant in the crude isosorbide mixture was in the range of from 250 to 900 ppm by weight. The stabilized crude isosorbide mixtures were then distilled in turn in a short path, jacketed distillation apparatus consisting of a 250 cc 3 neck boiling flask containing a PTFE magnetic stir bar in which one neck was fitted with a rubber septum, a thermocouple extended into the mixture being distilled from a central neck, and the third neck was equipped with the short path head leading to a boiling flask receiver maintained at 80 degrees Celsius. The boiling flask was immersed in an oil bath maintained at from 185 to 195 degrees Celsius, and distillation occurred under a vacuum pressure of less than 2 torr.

For this particular example, 4,4'-butylidenebis(6-t-butyl-m-cresol) (BBTC) was dissolved in 1-2 mL of absolute ethanol and added via pipette to a crude isosorbide product mixture, About 83 percent of the BBTC was determined by UPLC analysis to have distilled with the isosorbide in the distillate, which was clear and colorless with an APHA (neat) of 10.

About an 11 gram sample of the isosorbide distillate was added to a glass tube and capped with a septum. The glass tube was then submerged in a 200° C. oil bath for 1 hr under air. Approximately 0.5 g of the heated distillate sample was subsequently diluted with 2 mL of water and analyzed by UV/vis, demonstrating an APHA color value that was offscale.

The BBTC-stabilized distillate was further tested for color storage stability by thermal aging over a more extended period of time, in particular, by preparing typically five 10 mL headspace vials of each of the neat distillate and an 85% solution of the distillate in water in 0.5 gram sample portions. One vial of the set of five for the neat distillate or the 85% solution was set aside as the "time zero" data point. The time zero sample was diluted with 2 mL of water and analyzed.

For the neat distillate, the APHA color of the time zero sample was less than 1 by UV/vis. Formic acid concentration in the time zero sample was less than 5 ppm, while furfural concentration was less than 1 ppm. The four other vials of the neat distillate were then placed in an 85 deg C. oven under air, and one vial was removed at 7 days, another at 14 days, another at 21 days, and the last of the four at 28 days. Once removed from the oven, each sample was allowed to cool to room temperature and diluted with 2 mL of water. Each sample was then analyzed by UV/vis, UPLC, LC-MS, and GC. After 28 days, APHA color, measured as a 20% solution, was 191. Furfural and formic acid were measured at 298 ppm and 6,102 ppm, respectively.

For the 85% solution, by comparison, the APHA color values of the time zero and day 28, final diluted (20%) BBTC-stabilized solutions were less than 1 and off-scale (more than 500), respectively. The furfural concentration was less than 1 ppm initially, and 298 ppm in the final sample. The formic acid concentration initially was less than 5 ppm, but increased to 4264 ppm in the final sample.

The BBTC appeared to migrate out of the isosorbide bulk and form a layer on top near the walls of the vials. This was particularly a problem in the 85% solution as the stabilizer solubility was very poor.

Example 3

For this example, a more water-soluble additive, 6-hydroxy-2,5,7,8-tetramethylchromane-2-carboxylic acid (a vitamin E derivative sold by Hoffman-LaRoche, Nutley, N.J. under the trademark Trolox™) was added to a crude isosorbide product mixture prior to distillation of the same. About 26 percent of the Trolox™ additive was determined by UPLC analysis to have distilled with the isosorbide in the distillate, which was clear and colorless with an APHA (neat) of 15.

The Trolox™-stabilized distillate was tested for color storage stability by thermal aging over an extended period of time as in Examples 1 and 2. For the neat distillate, the APHA color of the time zero sample was 15 by UV/vis. Formic acid concentration in the time zero sample was less than 5 ppm, while furfural concentration was less than 1 ppm. After 28 days, APHA color, measured as a 20% solution, was over 500 (offscale). Furfural and formic acid were measured at 460 ppm and 3291 ppm, respectively.

For the 85% solution, by comparison, the APHA color values of the time zero and day 28, final diluted (20%) Trolox™-stabilized solutions were 5 and again more than 500, respectively. The furfural concentration was less than 1 ppm initially, and 512 ppm in the final sample. The formic acid concentration initially was less than 5 ppm, but increased to 3360 ppm in the final sample.

The rate of color formation in the stabilized samples was compared to a set of control vials containing distillate alone, and it was found that the stabilized samples indeed developed color more quickly than in the absence of the Trolox™ stabilizer.

Example 4

For this example, tert-butylhydroquinone (TBHQ) was added to a crude isosorbide product mixture to be distilled. Virtually a quantitative recovery of the additive was determined by UPLC analysis to have been realized in the distillate, which was clear and colorless.

The TBHQ-stabilized distillate was tested for color storage stability by thermal aging over an extended period of time as in previous examples. For the neat distillate, the APHA color of the time zero sample was 110 by UV/vis. Formic acid concentration in the time zero sample was less than 5 ppm, while furfural concentration was less than 1 ppm. After 28 days, APHA color, measured as a 20% solution, was 233. Furfural and formic acid were measured at 182 ppm and 3458 ppm, respectively.

For the 85% solution, by comparison, the APHA color values of the time zero and day 28, final diluted (20%) TBHQ-stabilized solutions were less than 1 and more than 500 (offscale), respectively. The furfural concentration was less than 1 ppm initially, and 257 ppm in the final sample. The formic acid concentration initially was less than 5 ppm, but increased to 770 ppm in the final sample.

Example 5

In this example, 2,6-dimethoxy-4-methylphenol (DMMP) was added to a crude isosorbide product mixture to be distilled. About 84 percent of the additive was determined by UPLC analysis to have been recovered in the distillate, which was clear and colorless with an APHA (neat) of 13.

About an 11 gram sample of the isosorbide distillate was added to a glass tube and capped with a septum. The glass tube was then submerged in a 200° C. oil bath for 1 hr under air. Approximately 0.5 g of the heated distillate sample was subsequently diluted with 2 mL of water and analyzed by UV/vis, demonstrating an APHA color value of 205.

The DMMP-stabilized distillate was then further tested for color storage stability by thermal aging over an extended period of time as in previous examples. For the neat distillate, the APHA color of the time zero sample was less than 15 by UV/vis. Formic acid concentration in the time zero sample was less than 5 ppm, while furfural concentration was not measured. After 28 days, APHA color, measured as a 20% solution, was 17. Formic acid was measured at 74 ppm.

For the 85% solution, by comparison, the APHA color values of the time zero and day 28, final diluted (20%) DMMP-stabilized solutions were 5 and 50, respectively. The furfural concentration was not measured. The formic acid concentration initially was less than 5 ppm, but increased to 63 ppm in the final sample.

Example 6

Butylated hydroxyanisole (BHA) was added in this example to a crude isosorbide product mixture to be distilled. About 63 percent of the additive was determined by UPLC analysis to have been recovered in the distillate, which was clear and colorless with art APHA (neat) of 14.

About an 11 gram sample of the isosorbide distillate was added to a glass tube and capped with a septum. The glass tube was then submerged in a 200° C. oil bath for 1 hr under air. Approximately 0.5 g of the heated distillate sample was subsequently diluted with 2 mL of water and analyzed by UV/vis, demonstrating art APHA color value of 222 as compared to a value that was offscale for a distillate lacking the BHA additive.

The BHA-stabilized distillate was then further tested for color storage stability by thermal aging over an extended period of time as in previous examples. For the neat distillate, the APHA color of the time zero sample was less than 15 by UV/vis. Formic acid concentration in the time zero sample was less than 5 ppm, while furfural concentration was not measured. After 28 days, APHA color, measured as a 20% solution, was 40. Formic acid was measured at 21 ppm.

For the 85% solution, by comparison, the APHA color values of the time zero and day 28, final diluted (20%) BHA-stabilized solutions were less than 1 and 30, respectively. The furfural concentration was not measured. The formic acid concentration initially was less than 5 ppm, but increased to 44 ppm in the final sample.

The invention claimed is:

1. A distillable composition of matter comprised of a) a crude dehydration product mixture from an acid-catalyzed dehydration of one or more hexitols which mixture includes at least an isohexide, and b) one or more antioxidant additives, at least one of which possesses sufficient volatility to at least partially co-distill with the isohexide on a distillation of the composition and is soluble in the isohexide under room temperature conditions.

2. A distillable composition according to claim 1, wherein at least 50 percent of the one or more antioxidant additives on a mass basis can be made to co-distill with the isohexide distillate using a wiped film evaporator.

3. A distillable composition according to claim 1, wherein the crude dehydration product is from an acid-catalyzed dehydration of sorbitol to make isosorbide, and the one or more antioxidant additives are selected from the group consisting of hindered phenols containing one or more methoxyl groups but no other functional groups other than alkyl groups, and mixtures of any of these.

4. A distillable composition according to claim 3, wherein the one or more antioxidant additives are selected from di-tert-butyl-4-methoxyphenol; butylated hydroxyanisole; 2,6-dimethoxy-4-methylphenol; 2,6-dimethoxyphenol and mixtures of any of these.

5. A distillable composition according to claim 4, wherein the one or more antioxidant additives comprise one or both of butylated hydroxyanisole and 2,6-dimethoxy-4-methylphenol.

6. A 100% molten isohexide-enriched product including one or more antioxidants selected from the group consisting of hindered phenols containing one or more methoxyl groups but no other functional groups other than alkyl groups, and mixtures of any of these, and having an initial APHA color according to ASTM D1209 as manufactured of 100 or less.

7. A 100% molten isohexide-enriched product according to claim 6, having an initial APHA color of 20 or less.

8. A 100% molten isohexide-enriched product according to claim 7, having an initial APHA color of 15 or less.

9. A 100% molten isohexide-enriched product according to claim 8, having an initial APHA color of 10 or less.

10. An 85% solution isohexide product including one or more antioxidants selected from the group consisting of hindered phenols containing one or more methoxyl groups but no other functional groups other than alkyl groups, and mixtures of any of these, and having an initial APHA color according to ASTM D1209 as manufactured of 100 or less.

11. An 85% solution isohexide product according to claim 10, having an initial APHA color of 20 or less.

12. An 85% solution isohexide product according to claim 11, having an initial APHA color of 15 or less.

13. An 85% solution isohexide product according to claim 12, having an initial APHA color of 10 or less.

14. A 100% molten isohexide-enriched product according to any one of claims 6 through 9, which after accelerated aging at 85 degrees Celsius for four weeks demonstrates an APHA color of 200 or less.

15. An 85% solution isohexide-enriched product according to any one of claims 10 through 13, which after accelerated aging at 85 degrees Celsius for four weeks demonstrates an APHA color of 250 or less.

16. A process for making one or more isohexides, comprising:
dehydrating one or more hexitols in the presence of an acid catalyst to form a crude dehydration product mixture comprising an isohexide;
adding one or more antioxidants to the crude dehydration product mixture, at least one of which possesses sufficient volatility to at least partially co-distill with the isohexide on a distillation of the crude dehydration product mixture and is soluble in the isohexide under room temperature conditions; and
distilling the crude dehydration product mixture containing the one or more antioxidants to yield an isohexide product including one or more antioxidants.

17. A process according to claim 16, further comprising contacting the crude dehydration product mixture with one or more ion exchange resins, with one or more ion exclusion resins or with both ion exchange and ion exclusion resins.

* * * * *